Figure 1:
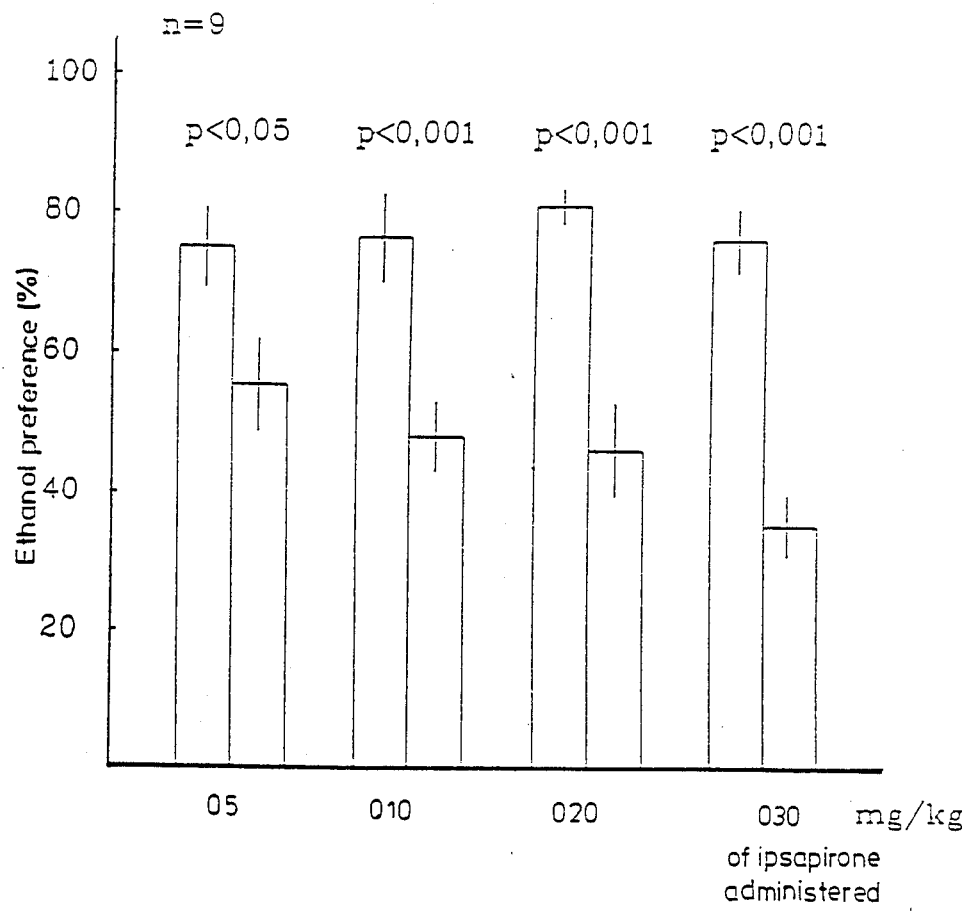

United States Patent [19]

Traber et al.

[11] Patent Number: 4,895,848

[45] Date of Patent: Jan. 23, 1990

[54] TREATMENT OF ALCOHOLISM USING 2-PYRIMIDINYL-1-PIPERAZINE DERIVATIVE

[75] Inventors: Jörg Traber, Lohmar; Klaus Opitz, Muenster, both of Fed. Rep. of Germany

[73] Assignee: Troponwerke GmbH & Co. KG., Cologne, Fed. Rep. of Germany

[21] Appl. No.: 227,962

[22] Filed: Aug. 3, 1988

[30] Foreign Application Priority Data

Aug. 21, 1987 [DE] Fed. Rep. of Germany ....... 3727879

[51] Int. Cl.$^4$ .......................................... A61K 31/495
[52] U.S. Cl. .................................................. 514/255
[58] Field of Search ........................................ 514/255

*Primary Examiner*—Stanley J. Friedman
*Attorney, Agent, or Firm*—Sprung, Horn, Kramer & Woods

[57] ABSTRACT

A method for the treatment of alcoholism and medicaments used for such treatment wherein patients receive an effective amount of a 2-pyrimidinyl-1-piperazine derivative of the formula

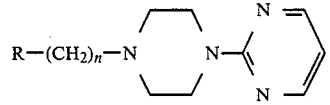

in which
n represents one of the numbers 2, 3, 4, 5 or 6, and
R represents

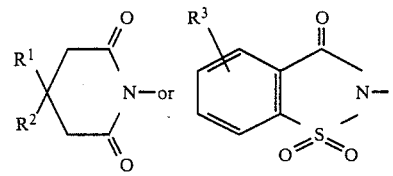

in which
$R^1$, $R^2$ and $R^3$ each independently denote hydrogen or lower alkyl, or salts thereof.

5 Claims, 1 Drawing Sheet

TREATMENT OF ALCOHOLISM USING 2-PYRIMIDINYL-1-PIPERAZINE DERIVATIVE

The invention relates to the use of 2-pyrimidinyl-1-piperazine derivatives for the preparation of medicaments for the treatment of alcoholism, and to corresponding medicaments.

EP-A No. 0,129,128 discloses 2-pyrimidinyl-1-piperazine derivatives and their action, which is essentially anxiolytic. Known active compounds from this class of substances are 8-[4-N-[-(2-pyrimidinyl)-1-piperazinyl]-butyl]-8-azaspiro[4.5]-decane-7,9-dione hydrochloride (according to INN: Buspirone Pharmacol. Biochem. Behav. 23, 687 to 694 (1985)), 4,4-dimethyl-1-[4-[4-(2-pyrimidinyl)-1-piperazinyl]butyl]-2,6-piperidinedione hydrochloride (according to INN: Gepirone Naunyn-Schmiedeberg's Arch. Pharmacol. 335, 454 to 464 (1987)) and 2-(4-(4-(2-pyrimidinyl)-1-piperazinyl)-butyl)-1,2-benzoisothiazol-3(2H)-one1,1-dioxide hydrochloride (according to INN: Ipsapirone Naunyn-Schmiedeberg's Arch. Pharmacol. 328, 467 to 470 (1985)).

It is disclosed in Alcohol 4 (1), 49 to 56 (1987) that monkeys with a preference for alcohol show a lower preference for alcohol in the time of a treatment with buspirone.

The use of 2-pyrimidinyl-1-piperazine derivatives of the formula

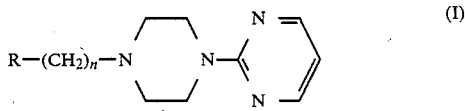

(I)

in which
n represents one of the numbers 2, 3, 4, 5 or 6, and
R represents one of the radicals

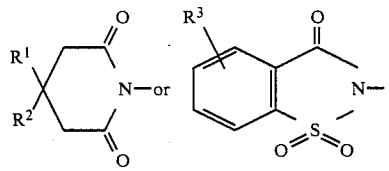

in which
$R^1$, $R^2$ and $R^3$ are identical or different and denote hydrogen or lower alkyl, and/or their salts, for the preparation of medicaments for the treatment of alcoholism has been found.

Corresponding medicaments are characterized by containing 2-pyrimidinyl-1-piperazine derivatives of the formula

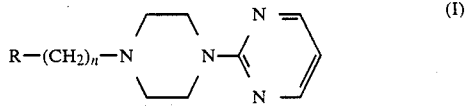

(I)

in which
n represents one of the numbers 2, 3, 4, 5 or 6, and
R represents one of the radicals

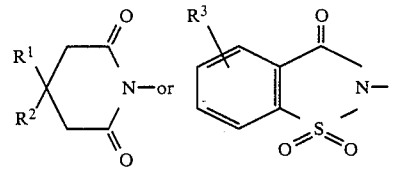

in which
$R^1$, $R^2$ and $R^3$ are identical or different and denote hydrogen or lower alkyl, and/or their salts.

Surprisingly, the effect of the 2-pyrimidinyl-1-piperazine derivatives according to the invention in the treatment of alcoholism is superior to that of buspirone. Within the scope of the formula (I), lower alkyl generally denote a straight-chain or branched hydrocarbon radical having 1 to, say, 6 carbon atoms. Examples which may be mentioned are methyl, ethyl, propyl, isopropyl, butyl, isobutyl, pentyl, isopentyl, hexyl and isohexyl. Methyl and ethyl are preferred.

Preferred 2-pyrimidinyl-1-piperazine derivatives of the formula (I) are those where
n represents one of the numbers 3 or 4, and
$R^1$, $R^2$ and $R^3$ denote hydrogen or methyl.

Salts which may be mentioned are pharmacologically acceptable salts such as the hydrochlorides.

Particularly preferred are ipsapirone and gepirone.

The preparation of the 2-pyrimidinyl-1-piperazine derivatives is known per se (DE-A No. 33 21 969) and can be effected, for example, by reaction of appropriate benzoisothiazoles with (piperazinyl)-pyrimidines.

The medicaments according to the invention generally contain 1 to 15% by weight, preferably 5 to 10% by weight, of 2-pyrimidinyl-1-piperazine derivatives.

It is, of course, possible for the medicaments according to the invention to contain further active compounds known per se.

The medicaments according to the invention can be converted in a known manner into the customary formulations such as tablets, coated tablets, pills, granules, aerosols, syrups, emulsions, suspensions and solutions, using inert, non-toxic, pharmaceutically suitable vehicles or solvents.

The formulations are prepared, for example, by extending the active compounds with solvents and/or vehicles, optionally with the use of emulsifiers and/or dispersing agents, and, for example when using water as a diluent, organic solvents can optionally be used as auxiliary solvents.

Examples of auxiliaries which may be mentioned are: water, non-toxic organic solvents such as paraffins (for example petroleum fractions), vegetable oils (for example groundnut/sesame oil), alcohols (for example ethyl alcohol or glycerol), vehicles such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally, parenterally, perlingually or intravenously. In the case of oral administration, the tablets can, of course, also contain, in addition to the vehicles mentioned, additives such as sodium citrate, calcium carbonate and dicalcium phosphate together with various additional substances such as starch, preferably potato starch, gelatine and the like. Furthermore, lubricants such as magnesium stearate, sodium lauryl sulphate and talc can also be used when making tablets. In the case of aqueous suspensions, the active compounds can be mixed with various flavour-improving agents or colorants in addition to the abovementioned auxiliaries.

In the case of parenteral administration, solutions of the active compounds, employing suitable liquid vehicles, can be used. In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 to 10 mg/kg, of body weight.

Nevertheless, it can at times be necessary to deviate from the amounts mentioned, and in particular to do so as a function of the body weight or of the nature of the administration method, of the individual behaviour towards the medicament, of the nature of its formulation and the time or interval over which administration takes place. Thus, it can suffice in some cases to manage with less than the abovementioned minimum amount, while in other cases the said upper limit must be exceeded. Where relatively large amounts are administered, it can be advisable to divide these into several individual administrations over the course of the day.

A useful agent for the medicamentous treatment of alcoholism is not yet known. The enzyme inhibitors disulfiram and nitrefazole give rise to an unpleasant reaction if the alcoholic treated with them drinks in spite of the ban.

In contrast to the latter substances, the 2-pyrimidinyl-1-piperazine derivatives according to the invention inhibit the voluntary alcohol consumption by those dependent on alcohol. In particular, the use of 2-pyrimidinyl-1-piperazine derivatives can prevent recidivism.

EXAMPLE 1

Preparation of 2-(4-(4-(2-pyrimidinyl)-1-piperazinyl)-butyl)-1,2-benzoisothiazol-3(2H)-one-1,1-dioxide

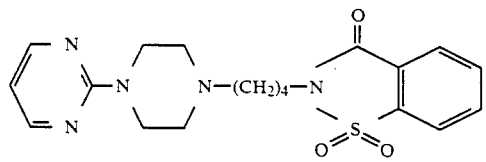

0.02 mole o& 2-(4-bromobutyl)-1,2-benzoisothiazol-3-(2H)-one 1,1-dioxide and 0.02 mole of 1-(2-pyrimidyl)piperazine are stirred with 0.02 mole of $K_2CO_3$ in 150 ml of absolute dimethylformamide (DMF) at 100° C. for 1 hour. The mixture is then concentrated. Water is added and the organic substance is taken up in methylene chloride ($CH_2Cl_2$). The dried $CH_2Cl_2$ phase is applied to a silica gel column and eluted with $CH_2Cl_2/CH_3OH$ (95:5).

Yield: 34% of theory; melting point: 138°–139° C.

EXAMPLE 2

Determination of the Activity

Ethanol-preferring rats are housed singly in large Makrolon cages under standardized conditions (12-hour light/dark rhythm, 23°±1° C.). Rearing feed, drinking water and 10% by volume ethanol are available in unlimited amounts to the animals but only during the dark period from 20.00 to 08.00 h. The substances to be investigated are administered once orally (2 ml/kg, stomach tube), specifically 30–20 min before the start of the dark period. The food vessels and the drinking bottles are weighed each morning, and the amounts consumed are determined. The measure used of the preference is the amount of alcohol (10% by volume) drunk as a percentage of the total intake of liquid. The consumptions measured after administration of a test substance are compared with the mean consumptions on the three preceding days (preliminary period). Table 1 shows the particular change in the total intake of liquid and the relative consumption of alcohol (10% by volume ethanol) as a percentage of the mean figures determined during the three-day preliminary period in each case. Student's t test for paired values is used for statistical calculations.

TABLE 1

Ingestive behaviour of eight male ethanol-preferring rats

| Substance | Dose (mg/kg oral) | Change in the total intake of liquid (%) | Change in the relative alcohol consumption (%) |
| --- | --- | --- | --- |
| Ipsapirone | 20 | +30.9*** | −43.1*** |
| Gepirone | 20 | +15.3** | −49.8*** |
| Buspirone | 20 | +1.6 ns | −1.6 ns |

**p <0.01
***p <0.001

The data show a marked increase in the total intake of liquid for ipsapirone and for gepirone, but this is accompanied by a large and highly significant decrease in the relative alcohol consumption. Accordingly, after administration of ipsapirone or gepirone there is a great reduction in the preference of the rats for alcohol. Buspirone shows no significant effect.

The FIGURE shows the ethanol preference of male rats before and after a single oral administration of ipsapirone. Dosages used were 5, 10, 20 and 30 mg/kg. It is clear from the FIGURE that administration of ipsapirone caused a marked decrease in the preference for alcohol.

What is claimed is:

1. A method of treating alcoholism comprising administering to a patient who is an alcoholic an effective amount of a 2-pyrimidinyl-1-piperazine derivative of the formula

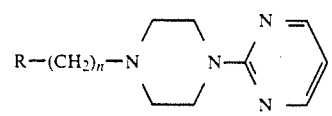

in which n represents one of the numbers 2, 3, 4, 5 or 6, and
R represents

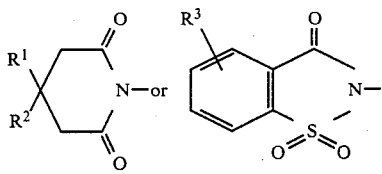

in which

R¹, R² and R³ each independently denote hydrogen or lower alkyl, and/or the salts thereof.

2. A method according to claim 1, wherein R¹, R² and R³ each independently denote hydrogen or $C_1$-$C_6$-alkyl.

3. A method according to claim 1, wherein n represents 3 or 4 and R¹, R² and R³ each independently denote hydrogen or methyl.

4. A method according to claim 1, wherein the 2-pyrimidinyl-1-piperazine derivative is 2-(4-(4-(2-pyrimidinyl)-1-piperazinyl)-butyl-1,1-benzoisothiazol-3(2H)-one 1,1-dioxide.

5. A method according to claim 1, wherein the -pyrimidinyl-1-piperazine derivative is 4,4-dimethyl-1-[4-[4-(2-pyrimidinyl)-1-piperazinyl]butyl]-2,6-piperidinedione.

* * * * *

UNITED STATES PATENT AND TRADEMARK OFFICE
CERTIFICATE OF CORRECTION

PATENT NO. : 4,895,848

DATED : January 23, 1990

INVENTOR(S) : Traber et al.

It is certified that error appears in the above-identified patent and that said Letters Patent is hereby corrected as shown below:

Col. 6, claim 5, line 12    Delete " -pyrimidinyl-1- " and substitute -- 2-pyrimidinyl-1- --

Signed and Sealed this

Second Day of July, 1991

Attest:

HARRY F. MANBECK, JR.

Attesting Officer

Commissioner of Patents and Trademarks